United States Patent [19]

Webb, Jr., deceased et al.

[11] Patent Number: 4,543,237
[45] Date of Patent: Sep. 24, 1985

[54] APPARATUS FOR CONTINUOUSLY MEASURING ACID GRAVITY IN A HYDROCARBON-ACID SYSTEM

[76] Inventors: Orlando Webb, Jr., deceased, late of Lee's Summit, Mo.; by Carlene M. Webb, representative, R.R. 4, F-12, Lee's Summit, (Jackson County), Mo. 64063

[21] Appl. No.: 403,027

[22] Filed: Jul. 29, 1982

[51] Int. Cl.$^4$ ............................ G05D 7/00; G05D 9/00
[52] U.S. Cl. ................................... 422/62; 250/357.1; 422/111; 436/55
[58] Field of Search ................ 585/715, 716; 250/308, 250/357.1, 358.1; 73/438, 439; 422/62, 106, 111, 193, 234, 230; 436/55

[56] References Cited

U.S. PATENT DOCUMENTS

| | | | |
|---|---|---|---|
| 2,799,645 | 7/1957 | Musgrove | 210/801 |
| 3,133,975 | 5/1964 | Brewer et al. | 585/716 |
| 3,170,769 | 2/1965 | Stiles et al. | 422/234 |
| 3,613,456 | 10/1971 | Hopfe et al. | 73/439 |
| 3,625,655 | 12/1971 | Culp et al. | 422/62 |
| 3,726,941 | 4/1973 | Randall et al. | 585/716 |
| 3,910,771 | 10/1975 | Chapman | 422/230 |
| 4,006,635 | 2/1977 | Khoi | 73/439 |
| 4,046,516 | 9/1977 | Burton et al. | 585/716 |

Primary Examiner—Barry S. Richman
Assistant Examiner—C. M. Delahunty
Attorney, Agent, or Firm—Litman, Day and McMahon

[57] ABSTRACT

A method and apparatus for measuring the acid gravity in an inorganic acid-organic fluid system permits constant monitoring of the acid gravity thus allowing the acid strength to be maintained at an optimum level. Particularly in a system such as an alkylation reactor, where product quality is dependent upon acid strength, the acid gravity measuring method and apparatus assures high product quality. A collecting vessel receives the inorganic acid-organic fluid mixture and the acid gravitates from the organic fluid in a disengaging chamber. The acid then enters an acid-analyzing section which includes acid gravity measuring means for determining the specific gravity of the separated acid. By continuously draining the fluid from the disengaging chamber and the acid-analyzing section, fresh fluid can be continuously introduced and the acid gravity continuously analyzed. In the case of an alkylation reactor, the acid gravity measuring means is coupled with valve means disposed in the acid supply line to the reactor. The quantity of make-up acid introduced into the reactor can thus be automatically increased or decreased in response to the measured specific gravity of the acid received in the collecting vessel, and the acid level in the reactor maintained in an optimum level at all times.

4 Claims, 5 Drawing Figures 4,543,237

APPARATUS FOR CONTINUOUSLY MEASURING ACID GRAVITY IN A HYDROCARBON-ACID SYSTEM

BACKGROUND OF THE INVENTION

This invention relates to apparatus for measuring the specific gravity of a liquid and, more particularly, to a method and apparatus for continuously monitoring the acid gravity in an inorganic acid-organic fluid system.

Many commercial reaction processes require the presence of an inorganic acid catalyst. For example, in petroleum refining, alkylation is widely used to convert olefinic hydrocarbons to highly branched paraffinic hydrocarbons. Because there is inevitably a certain amount of contamination of the acid catalyst in the alkylation process, it is necessary to continuously introduce make-up acid into the alkylation reactor. The quantity of make-up acid which is added to the reactor is determined on the basis of the acid strength of the acid which is separated out from the product alkylate and partly returned to the reactor. This acid strength is determined by an operator withdrawing a sample of the acid and then measuring the specific gravity of the sample which is directly related to acid strength. An optimum acid strength is normally associated with a particular process. The quantity of make-up acid introduced into the alkylation reactor is either increased or decreased to maintain such an optimum concentration in accordance with acid strength analysis.

The primary disadvantage associated with previous analyzing procedures is that the analysis is generally not continuous and regardless of the skill of the operator, the quantity of make-up acid introduced is not maintained at an optimum level. When an operator using old procedures adds make-up acid in response to a low specific gravity reading, he invariably adds too much and an amount of excess acid is present in the reactor which excess eventually becomes wasted. On the other hand, when the operator determines that the quantity of acid in the reactor has exceeded the optimum level, he reduces the amount of make-up acid and often overcompensates thus resulting in acid deficiencies in the reactor which reduces the quality of the product alkylate.

OBJECTS OF THE INVENTION

Therefore the objects of the present invention are: to provide a method and apparatus for measuring the specific gravity of the acid catalyst exiting an alkylation reactor whereby the acid gravity in the product alkylate is continuously monitored and the supply of make-up acid to the reactor is automatically varied so as to optimize the acid gravity, thereby avoiding both the waste of excess acid or the reduced product quality resulting from acid deficiency; to provide a method and apparatus for measuring the acid gravity in an inorganic acid-organic fluid system which is generally not dependent upon the skill of an operator; to provide a method and apparatus measuring the acid gravity in an inorganic acid-organic fluid system wherein the acid gravity is continuously analyzed and the time-consuming step of batch collecting is eliminated; to provide a method and apparatus for measuring the acid gravity in an inorganic acid-organic fluid system wherein greater accuracy is possible as a result of the fact that the acid is continuously analyzed by automated equipment; to provide a method and apparatus for continuously analyzing the acid gravity in an alkylation reactor system and adjusting the quantity of make-up acid introduced into the reactor accordingly, whereby automated equipment reduces manpower requirements; and to provide an apparatus which is easy to manufacture and particularly well adapted for the intended use thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DESCRIPTION OF THE PREFERRED EMBODIMENTS

As required, detailed embodiments of the present invention are disclosed herein, however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
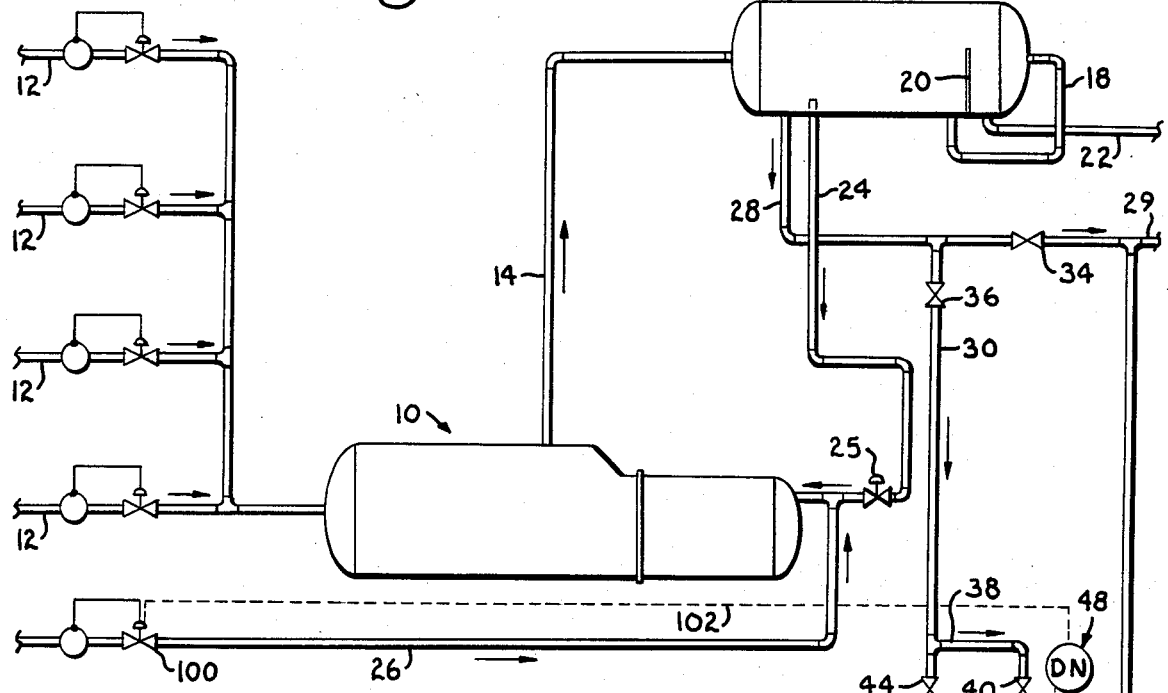
FIG. 1 is a schematic illustration of pertinent portions of an alkylation reactor system incorporating the method and apparatus for measuring acid gravity according to the present invention, with the front of the apparatus removed to show detail thereof.

Referring initially to FIG. 1, an alkylation reactor is designated generally by the numeral 10. It is to be understood that only those portions of the alkylation system which are pertinent to the present invention are shown in FIG. 1 and other portions, such as a refrigeration cycle would normally be present. The reactor 10 is supplied by a plurality of hydrocarbon feed streams 12 which bring olefins into the reactor. The olefins alkylate within the reactor thereby producing an alkylate product. The product exits from the reactor 10 in an inorganic acid-organic fluid mixture. The inorganic acid is an inorganic acid catalyst, such as preferably sulfuric acid, and the alkylation product is generally paraffinic hydrocarbons produced in the reactor. This acid-hydrocarbon mixture leaves the reactor 10 through a conduit 14 which communicates with an acid decanter or separator 16. The separator 16 is provided with a sight glass 18 for indicating the liquid level in the separator 16 to allow an operator or automatic controller to control the interface between separated acid and hydrocarbon layers which generally separate in the separator 16. The separator 16 also includes a vertical baffle 20 for assisting in the separation of the hydrocarbon phase from the acid phase of the product stream, generally by gravitational splitting of the acid-hydrocarbon mixture.

The hydrocarbon phase leaves the separator 16 through a line 22 and the bulk of the acid phase is recycled through a line 24 which communicates with the reactor 10 through control valves 25 which can be utilized to partially regulate level of the acid level in the separator 16. A make-up acid line 26 flow communicates with the line 24 to allow introduction of make-up acid from a source (not shown) to be added to the reactor 10 to maintain the acid strength at an optimum level at all times. Spent acid includes some functional acid but is removed from the remaining acid so as to remove impurities therewith and thereby maintain relatively good acid strength in the reactor. Spent acid removed from the system is basically replaced by make-up acid. The spent acid is allowed to gravitate to the bottom of the separator 16 where it is withdrawn through a line 28. Spent acid is delivered to storage or disposal which is not shown through line 29 which is a continuation of line 28.

A slip stream conduit 30 provides means for delivering a sample of the spent acid from line 28 to an acid gravity measuring apparatus designated generally by the numeral 32. Valves 34 and 36 in the line 28 and the stream conduit 30 are adjusted to assure a constant flow of acid into the apparatus 32. The stream conduit 30 is branched into a first line 38 having a control valve 40 and communicating with the apparatus 32, and a second line 42 which is open at one end and is provided with a control valve 44. The valve 44 is normally closed and the valve 40 is normally open to direct the entire slip stream of acid into the apparatus 32. However, when it is desired to manually check a sample of the acid, the valve 44 can be opened to withdraw a sample. The apparatus 32 comprises a collecting vessel 46, the construction of which is shown in detail in FIG. 2, and an acid gravity measuring device 48.

Figure 2:
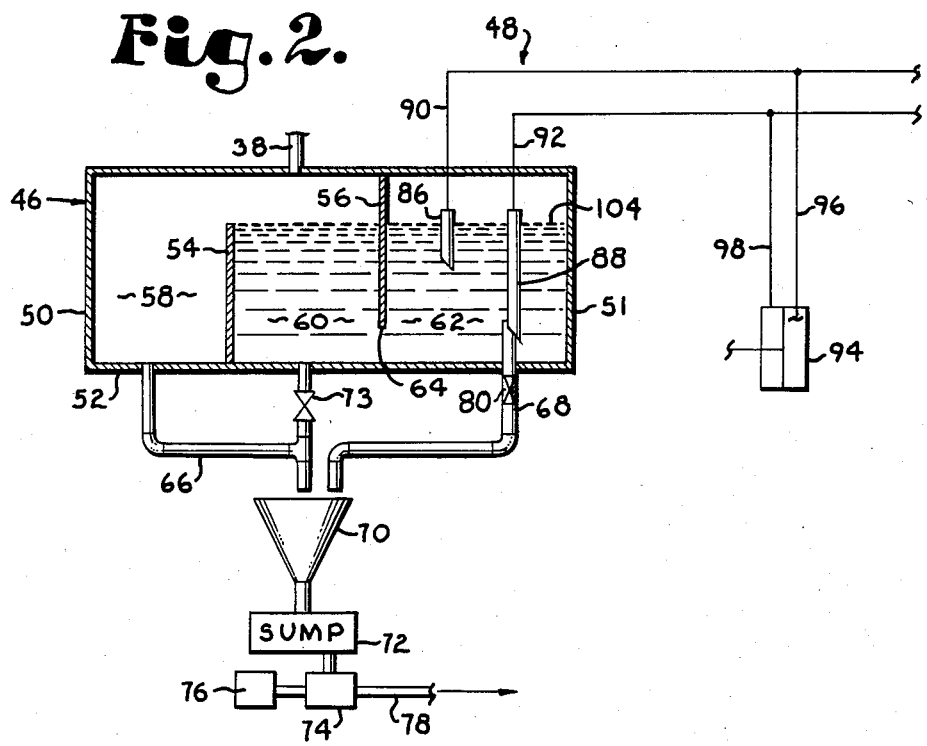
FIG. 2 is an enlarged view of the acid gravity measuring apparatus of the present invention with its cover and front removed.
Figure 3:
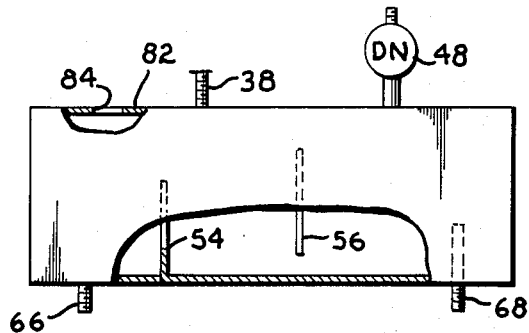
FIG. 3 is a side elevational view of the apparatus shown in FIG. 2 with the cover in place and front partially broken away.

Referring to FIG. 2, the vessel 46 comprises a pair of vertical side walls 50 and 51 which are integral and sealably connected with a bottom 52. First and second baffles 54 and 56 each of which is parallel to the walls 50 and 51 divide the vessel 46 into an organic fluid receiving section 58, a disengaging chamber 60 and an acid-analyzing section 62. The chamber 60 communicates with the section 62 as a result of an opening 64 between the baffle 56 and the bottom 52. The baffle 56 helps to retain organic fluid that enters the vessel 46 with the acid in the chamber 60 so that the organic fluid gravitates to the top of chamber 60 and overflows baffle 54 into chamber 58, rather than entering chamber 62 and possibly interferring with density determinations of the acid in chamber 62. Each of the sections 58 and 62 is provided with drainage structure 66 and 68 respectively for continuously withdrawing fluid from these sections and depositing the same in a funnel 70 which communicates with a sump 72, so as to collect the fluid. A drain conduit 77 is provided to allow drainage of sections 60 and 62 for cleaning or the like by operation of a valve 73 in conduit 77. Conduit 77 flow connects with the structure 66 to drain into the funnel 70. Liquid is withdrawn from the sump 72 by a sump pump 74 driven by a motor 76 which returns the acid from the slip stream to the line 28 through a line 78. A valve 80 in the drainage structure 68 is of a flow control type and assures that the volume of the liquid in the section 62 remains at a proper level. The collecting vessel 46 is normally enclosed by a cover 82 (FIG. 3). The cover 82 is provided with an opening 84 for venting the interior of the vessel 46. The opening 84 may communicate directly with the atmosphere or be coupled with an overflow tank through an appropriate connecting line. Overflow protection is also provided for the acid decanter 16 through line 85.

The acid gravity measuring device 48 is a conventional piece of specific gravity measuring equipment of the type well known to those skilled in the art. A machine of this type has been available from the Bailey Meter Company of Wickliffe, Ohio under the designation "LJ 23-Model 02". The device 48 utilizes a pair of bubble tubes 86 and 88 of different lengths which are disposed in the acid-analyzing section 62. Air is supplied to the tubes 86 and 88 by air lines 90 and 92 respectively and the pressure differential between the back pressure of the air bubbling from the tube 88 and the back pressure of the air bubbling from the tube 86 is measured by a diaphragm mechanism designated generally by the numeral 94. This occurs as a result of the diaphragm 94 being coupled with the air lines 90 and 92 through tie lines 96 and 98 respectively.

A valve 100 in the make-up acid line 26, which valve controls the quantity of make-up acid introduced into the reactor 10, is preferably automatically operated by the mechanism 94 as a result of a coupling mechanism 102. The coupling mechanism 102 may be of any type well known to those skilled in the art such as an air or electrical signal line. The electrical or pneumatic signal generated by the mechanism 94 can be utilized to drive a recorder in addition to controlling the valve 100.

In operation, spent acid from the acid decanter 16 is directed to the apparatus 32 through slip stream conduit 30 and line 38. As was previously explained, the valve 44 is normally closed and the valves 40 and 80 are adjusted to assure a continuous flow of fluid through the apparatus 32 while maintaining a suitable acid level 104. The acid level 104 must be above the highest point where air escapes from the tubes 86 and 88 in order for the acid gravity measuring device to function. It is foreseen that many of the valves shown, such as valve 80, could be automatically controlled by suitable flow or level controllers known to those skilled in the art. In general, the flow of fluid into the vessel 46 should be approximately one pint/minute. The spent acid contains a certain retained quantity of the hydrocarbon produced in the alkylation reaction even after separation in the decanter 16 and the hydrocarbon sulfuric acid mixture is thus introduced into the disengaging chamber 60 wherein the heavier acid component of the mixture will gravitate to the bottom of the chamber. The light hydrocarbon will spill over the baffle 54 into the organic fluid receiving section 58. Because of the general flow of fluid in the direction of the drainage structure 68, the acid from the chamber 60 will move through the opening 64 and into the acid-analyzing section 62. In the section 62, the acid gravity is continuously monitored by the device 48. When the acid gravity measured by the device 48 falls to a level indicating that the acid strength in the reactor is below an optimum level, the valve 100 is opened further to introduce additional quantities of the make-up acid. When the acid gravity measured by the device 48 indicates that the acid strength in the reactor 10 is above the level required for optimum production of alkylate, such that excess acid is being disposed of through conduit 29, the valve 100 is closed further to reduce the quantity of make-up acid being introduced and increase the flow of acid returning to the reactor 10 through line 24. Because the acid in the section 62 is continuously analyzed and the valve 100 automatically adjusted in response to the requirements of the system, the acid strength in the reactor is maintained at a substantially constant level throughout the reaction process.

Figure 5:
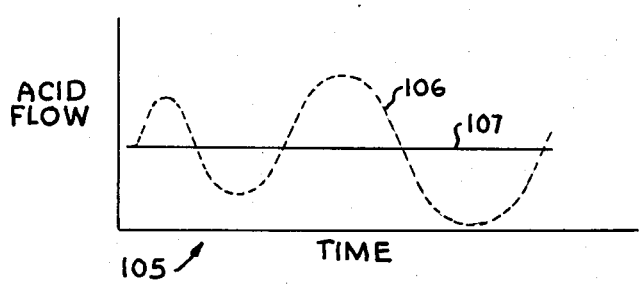
FIG. 5 is a graph illustrating the acid flow into an alkylation reactor as a function of time for both the present invention and the prior art methods.

The advantages of the apparatus of the present invention are illustrated in the graph 105 of FIG. 5 wherein the acid flow has been plotted as a function of time. The broken line 106 which is characterized by peaks and valleys is generally typical of the acid flow volume utilizing the control methods of the prior art. The peaks in this curve are attributable to the presence of excess acid as a result of an operator overcompensating for an acid deficiency, and the valleys in the curve are attributable to acid deficiencies. On the other hand, the solid line 107 in the graph 105 of FIG. 5 is generally indicative of the acid flow volume when the apparatus of the present invention is employed. The acid flow graph 105 in this case is approximately a straight line with an optimum quantity of acid being present at all times and both excess acid and acid deficiencies being normally avoided.

Figure 4:
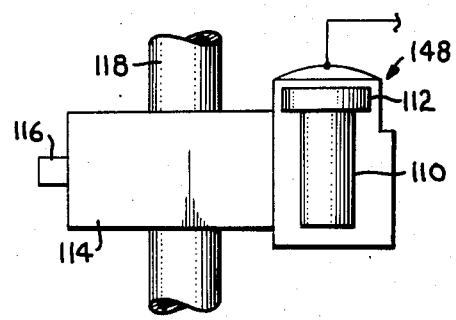
FIG. 4 is a schematic illustration of an alternative form of device for measuring the acid gravity.

An alternative device for measuring the specific gravity of the acid in the section 62 is schematically shown in FIG. 4 and designated generally by the numeral 148. The device 148 is of the type that has been available under the name "Ohmart Nuclear Density Gages -Model CP" from The Ohmart Corporation of Cincinnati, Ohio. Those skilled in the art will be generally familiar with specific gravity measuring devices of this type and will recognize that they include a radiation detecting cell 110, an amplifier 112, a sample receiving section 114 and a source of radioactivity 116. With the device 148, the sample from the section 62 is introduced into the section 114 by means of a line 118, the output of which will communicate with the drainage structure 68. Operation of the apparatus of the invention is the same as previously explained for the device 48 when using the alternative device 148 for measuring the acid gravity. In this instance, however, radiation from the source 116 passes through the line 118 and the material moving inside thereof. Some radiation is absorbed by the material generally in porportion to the density of this material. Radiation not absorbed is detected by the cell 110 and this residual radioactive energy is converted into an electrical current and amplified to provide an electrical signal.

Manifestly, the present invention also contemplates a method of measuring the specific gravity of the acid phase of an inorganic acid-organic fluid system. In carrying out the method, a sample of the inorganic acid-organic fluid mixture is first collected by continuously introducing a quantity of the mixture into a separating zone, such as chamber 60, and separating the organic fluid from the acid by allowing the latter to gravitate from the flow. Next, the acid is channeled into an analyzing zone, such as chamber 62, wherein the specific gravity of the acid is measured. Simultaneously, acid is removed from the analyzing zone to permit a continual flow of fresh acid into this zone. The specific gravity is preferably continuously monitored and when this is done the method of the invention is particularly adapted for use in controlling the quantity of acid introduced into an alkylation reactor of the type requiring a quantity of make-up acid to be added during operation of the reactor. To this end, the inventive method encompasses the additional step of automatically increasing or decreasing the quantity of make-up acid added to an alkylation reactor in response to variations in the specific gravity of the acid as sensed in the acid-analyzing zone.

It is to be understood that while certain forms of the present invention have been illustrated and described herein, it is not to be limited to the specific forms or arrangement of parts described and shown.

Having thus described the invention, what is claimed and desired to secure by Letters Patent is:

1. In an acid catalyzed reactor having means for controllably introducing a quantity of acid catalyst into said reactor; said reactor being of the type requiring a quantity of make-up acid to be added to said reactor through an acid supply line during continuous operation of said reactor for optimum production of alkylate the improvement being wherein said means for controllably introducing acid into said reactor comprises:

(a) a collecting vessel for receiving a quantity of product from the reactor; said vessel having a bottom and spaced side walls extending upward from said bottom; said side walls being sealably joined at respective ends thereof with each other and with said bottom so as to be fluid containing;

(b) structure coupling said reactor with said vessel for continuously delivering to said vessel a portion of the product having acid and organic fluid alkylate therein from said reactor;

(c) said vessel including a disengaging chamber positioned between said walls and operably allowing substantially all of said acid in the product to gravitate to a lower portion of the chamber so as to separate the product entering said disengaging chamber into separated acid and separated alkylate; said coupling structure delivering the product portion directly into said disengaging chamber;

(d) said vessel further including an acid-analyzing section communicating with said chamber to receive the separated acid; said acid-analyzing section being separated from said disengaging chamber by first baffle means connected to said vessel walls and operably cooperating with said vessel bottom to allow said separated acid to flow past said first baffle means from said disengaging chamber to said acid-analyzing section and further operably blocking flow of said separated alkylate from said disengaging chamber to said acid analyzing section;

(e) said vessel also including an organic fluid receiving section communicating with said disengaging chamber to receive the separated alkylate therefrom; said disengaging chamber being separated from said organic fluid receiving section by second baffle means cooperating with said vessel bottom to allow said separated alkylate to flow from said disengaging chamber to said organic fluid receiving section and operably blocking flow of said separated acid between said disengaging chamber and said organic fluid receiving section;

(f) acid gravity measuring means disposed in said acid-analyzing section for continuously sensing the specific gravity of the separated acid;

(g) first outlet means from said acid analyzing section for discharge of said separated acid therefrom after sensing the specific gravity of said separated acid;

(h) second outlet means cooperating with said organic fluid receiving section for discharge of said separated alkylate therefrom; and (i) valve means disposed in an acid supply line and operably coupled with said measuring means for providing increases or decreases in the flow of make-up acid into said reactor in response to variations in the specific gravity of the separated acid as sensed by said gravity measuring means whereby the quantity of acid in the reactor is maintained at an optimum level.

2. An apparatus for collecting an inorganic acid-organic fluid sample to allow for measuring of the acid gravity in an inorganic acid-organic fluid system, said apparatus comprising:

(a) a vessel having spaced side walls and a bottom joined to retain fluid therein; said vessel for receiving an inorganic acid-organic fluid sample; said vessel including first and second spaced generally vertical baffles; each of said baffles being connected to said walls and defining therebetween and within said vessel a disengaging chamber, an acid-analyzing section, and an organic fluid receiving section;

(b) means for delivering said fluid into said disengaging chamber such that the fluid sample is originally received in said disengaging chamber; said first and second baffles being sealably secured near opposite ends thereof respectively to each of said side walls;

(c) said first baffle being positioned between said chamber and said acid-analyzing section and being spaced from the bottom of said vessel for providing flow communication from the chamber to the acid-analyzing section whereby the acid is operably allowed to gravitate to the bottom of said chamber so as to separate the acid from the organic fluid and thereafter to enter said acid-analyzing section;

(d) acid gravity measuring means positioned to measure acid gravity within said acid-analyzing section;

(e) said second baffle being positioned between said chamber and said organic fluid receiving section and having an upper edge that is positioned below the height of both the first baffle and the side walls of the vessel whereby when said chamber is filled with an acid-organic fluid mixture the organic fluid operably spills over said second baffle and into said organic fluid receiving section;

(f) first outlet means for discharge of said acid from said acid-analyzing section after measurement of the gravity thereof;

(g) second outlet means for discharge of said organic fluid from said organic fluid receiving section; and (h) whereby said apparatus allows a sample of said acid to be operably continuously replaced with a fresh sample in said acid-analyzing section to provide for continuous analysis of said acid.

3. An apparatus for measuring the acid gravity in an inorganic acid-organic fluid from an alkylation reactor, comprising:

(a) a collecting vessel for receiving and separating an inorganic acid-organic containing fluid; said vessel having a bottom, generally vertical spaced side walls extending upwardly from said bottom and being sealed therewith, a cover extending between said walls and spaced from said bottom; said walls being joined by opposite respective ends thereof to define a fluid enclosure with said bottom, and first and second baffle means within said vessel; said first and second baffle means being spaced from one another and forming therebetween a centrally located disengaging chamber; said first baffle means cooperating with said side walls to form an acid measuring chamber therebetween and said second baffle means cooperating with side walls to form an organic fluid collection chamber; said first baffle means having a lower end in close proximity to but spaced away from said bottom wall to allow a separated acid component from the disengaging chamber to flow thereunder and said second baffle means being attached to said bottom and being spaced from said cover so as to operably allow separated organic fluid only to flow thereover; said first and second baffles generally extending between and being connected to said walls;

(b) said vessel having inlet means connected to said cover and positioned relative to said disengaging chamber so as to feed the inorganic acid-organic fluid from an alkylation reactor directly into said disengaging chamber such that the separated acid gravitates to the bottom thereof to flow under said first baffle means into said acid measuring chamber;

(c) acid gravity measuring means operably positioned so as to determine the specific gravity of the separated acid in said acid measuring chamber; and (d) outlet means for each of said chambers at a lower end thereof for discharging the separated acid and separated organic fluid from said vessel.

4. Apparatus as set forth in claim 3 wherein:

(a) each of said outlet means includes a continuous drainage structure for continuously removing said organic fluid and said acid from said respective chambers associated therewith, whereby said separated acid may be continuously replaced with a newly separated acid and said organic fluid may be continuously removed from said vessel.

* * * * *